United States Patent
Okamura et al.

(10) Patent No.: US 9,326,749 B2
(45) Date of Patent: May 3, 2016

(54) ULTRASOUND DIAGNOSIS APPARATUS AND CONTROLLING METHOD

(75) Inventors: Yoko Okamura, Nasushiobara (JP); Naohisa Kamiyama, Otawara (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 580 days.

(21) Appl. No.: 13/435,346

(22) Filed: Mar. 30, 2012

(65) Prior Publication Data

US 2012/0253181 A1   Oct. 4, 2012

(30) Foreign Application Priority Data

Apr. 1, 2011 (JP) ................................ 2011-081986
Feb. 28, 2012 (JP) ................................ 2012-041505

(51) Int. Cl.
*A61B 8/14* (2006.01)
*A61B 8/08* (2006.01)
*A61B 8/00* (2006.01)

(52) U.S. Cl.
CPC .............. *A61B 8/0841* (2013.01); *A61B 8/5246* (2013.01); *A61B 8/46* (2013.01); *A61B 8/486* (2013.01); *A61B 8/488* (2013.01)

(58) Field of Classification Search
CPC ...... A61B 8/0841; A61B 8/5246; A61B 8/46; A61B 8/488; A61B 8/486
USPC ......... 600/437, 443, 459, 454, 466, 424, 461, 600/464, 439, 425, 462; 604/93.01, 19, 117
See application file for complete search history.

(56) References Cited

U.S. PATENT DOCUMENTS 9,119,558 B2    9/2015  Yoshida et al.
2002/0156376 A1* 10/2002 Wang et al. .................. 600/439
(Continued)

FOREIGN PATENT DOCUMENTS

JP    2006-320378 A   11/2006
JP    2007-054504 A    3/2007
(Continued)

OTHER PUBLICATIONS

"Advanced Needle Visualization", Advanced needle visualization for Ultrasound Images, SonoSite, Inc., www.sonosite.org/needlevisualization.
(Continued)

*Primary Examiner* — Long V Le
*Assistant Examiner* — Colin T Sakamoto
(74) *Attorney, Agent, or Firm* — Yoshida & Associates, LLC

(57) ABSTRACT

An ultrasound diagnosis apparatus includes: a scan controlling unit that exercises control to perform a first scanning process by transmitting an ultrasound wave in a first direction and a second scanning process by transmitting an ultrasound wave in each of a plurality of directions; an image generating unit that generates a first ultrasound image and second ultrasound images from the first and the second scanning processes, respectively; an image generation controlling unit that has a needle image generated, based on an analysis result on the brightness distribution of each member of a group of images based on the first ultrasound image and the second ultrasound images or an analysis result on the brightness distribution of each of the second ultrasound images; an image synthesizing unit that generates a synthesized image from the first ultrasound image and the needle image; and a display controlling unit that displays the synthesized image.

12 Claims, 11 Drawing Sheets

(56) References Cited

U.S. PATENT DOCUMENTS

| | | | |
|---|---|---|---|
| 2002/0173719 A1 | 11/2002 | Zhao et al. | |
| 2003/0135119 A1* | 7/2003 | Lee et al. | 600/461 |
| 2004/0133168 A1* | 7/2004 | Salcudean et al. | 604/164.13 |
| 2007/0016035 A1* | 1/2007 | Hashimoto | 600/437 |
| 2007/0167769 A1* | 7/2007 | Ikuma et al. | 600/437 |
| 2007/0167801 A1* | 7/2007 | Webler et al. | 600/459 |
| 2009/0099544 A1* | 4/2009 | Munrow et al. | 604/506 |
| 2010/0298704 A1* | 11/2010 | Pelissier et al. | 600/443 |
| 2011/0054320 A1* | 3/2011 | Nishihara et al. | 600/443 |
| 2011/0190632 A1* | 8/2011 | Kim et al. | 600/443 |

FOREIGN PATENT DOCUMENTS

| | | |
|---|---|---|
| JP | 2008-012150 A | 1/2008 |
| JP | 2010-183935 A | 8/2010 |

OTHER PUBLICATIONS

Chinese Office Action with its English translation for Chinese Patent Application No. 201210093673.7 mailed on Dec. 12, 2013.

Japanese Office Action with its English Summary for the corresponding Japanese Patent Application No. 2012-041505 mailed on Dec. 8, 2015.

* cited by examiner

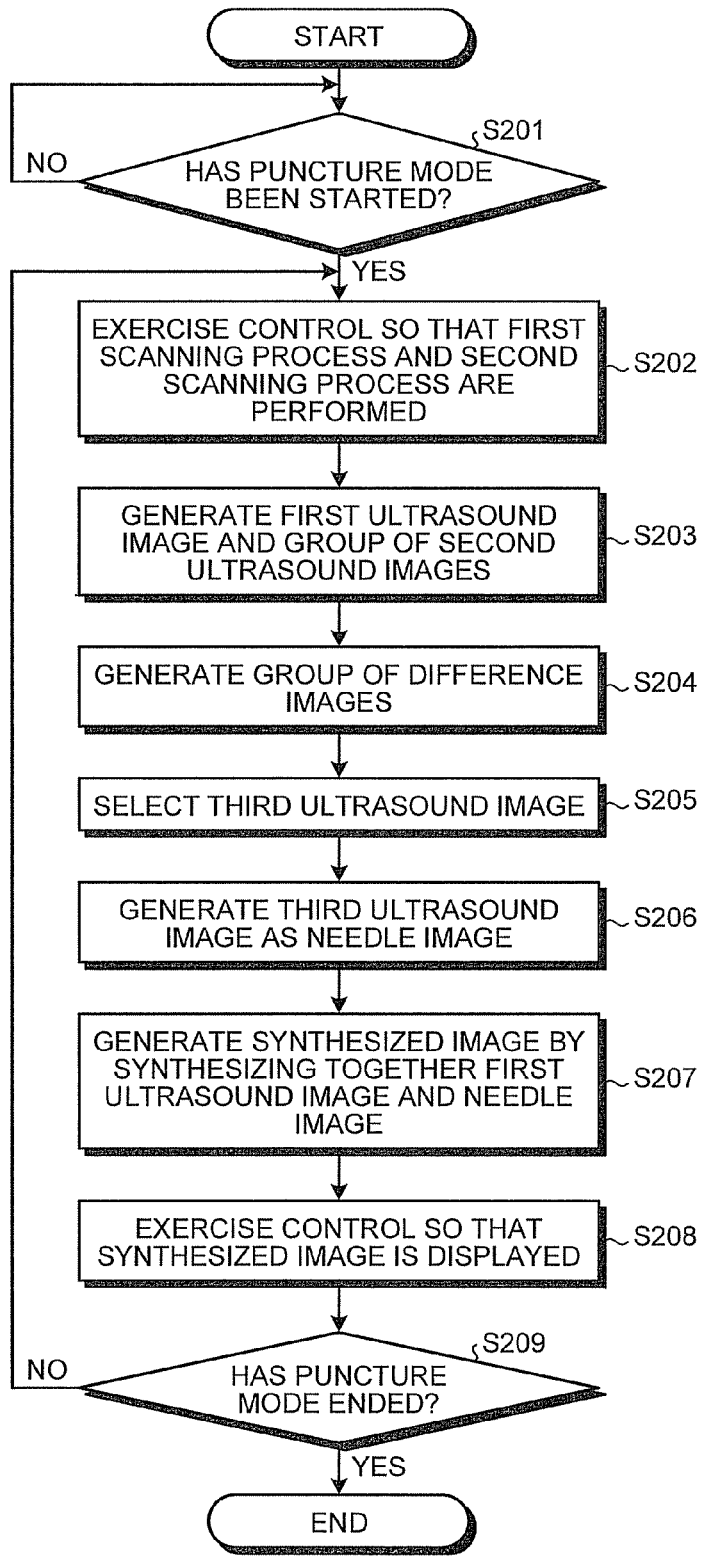

ULTRASOUND DIAGNOSIS APPARATUS AND CONTROLLING METHOD

CROSS-REFERENCE TO RELATED APPLICATIONS

This application is based upon and claims the benefit of priority from Japanese Patent Application No. 2011-081986, filed on Apr. 1, 2011; and Japanese Patent Application No. 2012-41505, filed on Feb. 28, 2012, the entire contents of all of which are incorporated herein by reference.

FIELD

Embodiments described herein relate generally to an ultrasound diagnosis apparatus and a controlling method.

BACKGROUND

Conventionally, ultrasound diagnosis apparatuses have often been used for performing a test on a tissue in a subject's body and providing Radio Frequency Ablation (RFA) treatments where a puncture process is performed while using a puncture needle, because ultrasound diagnosis apparatuses are capable of displaying an ultrasound image captured immediately underneath an ultrasound probe in a real-time manner. Depending on where the lesion is positioned and the angle at which a puncture needle is inserted, it can be difficult to see the puncture needle in some situations. In those situations, the puncture process is performed while checking on how the tissue moves when, for example, the puncture needle is moved around.

To cope with those situations, a technique is known these days by which, to improve the visibility of a puncture needle during a puncture process, an ultrasound beam is radiated perpendicularly to the puncture needle by performing an oblique scanning process, so as to generate an ultrasound image (a needle image) in which the puncture needle is rendered with a high level of brightness. Further, another technique is also known by which, without performing the oblique scanning process, a regular ultrasound scanning process is performed so as to generate, in addition to a needle image, an ultrasound image (a subject-body image) in which a tissue in the subject's body is rendered and so as to generate and display a synthesized image obtained by synthesizing together the needle image and the subject-body image. According to this technique, when the synthesized image is generated, one or more of the following processes are performed: a process to add together the needle image and the subject-body image; a process to superimpose the images with one another by averaging the pixel values for each of the pixels; and a process to hold the maximum value of brightness levels for each of the pixels (a maximum brightness value holding process or a Max-Hold process).

It should be noted, however, that the tissue in the subject's body rendered in the ultrasound image generated by performing the oblique scanning process has lower image quality than in an image obtained by performing a non-oblique scanning process, due to a side-lobe effect or the like. For this reason, although the visibility of the puncture needle in the synthesized image is improved to some extent, the diagnosability using the synthesized image is lower because it is not possible to perform a substantive observation on a lesion in the tissue in an optimal manner. In other words, a phenomenon occurs where, although the puncture needle is easier to see because the ultrasound beam is perpendicularly applied to the puncture needle, information about the tissue in the subject's body becomes degraded due to occurrence of, for example, a grating side-lobe caused by problems related to the shape of the beam or the like.

BRIEF DESCRIPTION OF THE DRAWINGS

FIG. 11 is a flowchart for explaining a process performed by an ultrasound diagnosis apparatus according to the third embodiment;

DETAILED DESCRIPTION

According to one embodiment, an ultrasound diagnosis apparatus includes a scan controlling unit, an image generating unit, an image generation controlling unit, an image synthesizing unit and a display controlling unit. The scan controlling unit is configured to, when performing an ultrasound scanning process on a subject into whom a puncture needle has been inserted, cause an ultrasound probe to perform a first scanning process by transmitting an ultrasound wave in a first direction with respect to a surface of a vibrator for a purpose of taking an image of a tissue of the subject and a second scanning process by transmitting an ultrasound wave in each of a plurality of directions with respect to the surface of the vibrator. The image generating unit is configured to generate a first ultrasound image by using a reflected wave received by the ultrasound probe during the first scanning process and to generate a group of second ultrasound images that are ultrasound images corresponding to the plurality of directions by using reflected waves received by the ultrasound probe during the second scanning process. The image generation controlling unit is configured to control the image generating unit so as to generate a needle image in which the puncture needle is rendered with a high level of brightness, based on an analysis result obtained by analyzing a brightness distribution of each member of a group of images based on the first ultrasound image and the group of second ultrasound images or based on an analysis result obtained by analyzing a brightness distribution of each member of the group of second ultrasound images. The image synthesizing unit configured to generate a synthesized image by synthesizing together the first ultrasound image and the needle image generated by the image generating unit. The display controlling unit configured to exercise control so that the synthesized image generated by the image synthesizing unit is displayed on a predetermined display unit.

In the following sections, exemplary embodiments of an ultrasound diagnosis apparatus will be explained in detail, with reference to the accompanying drawings.

Figure 1:
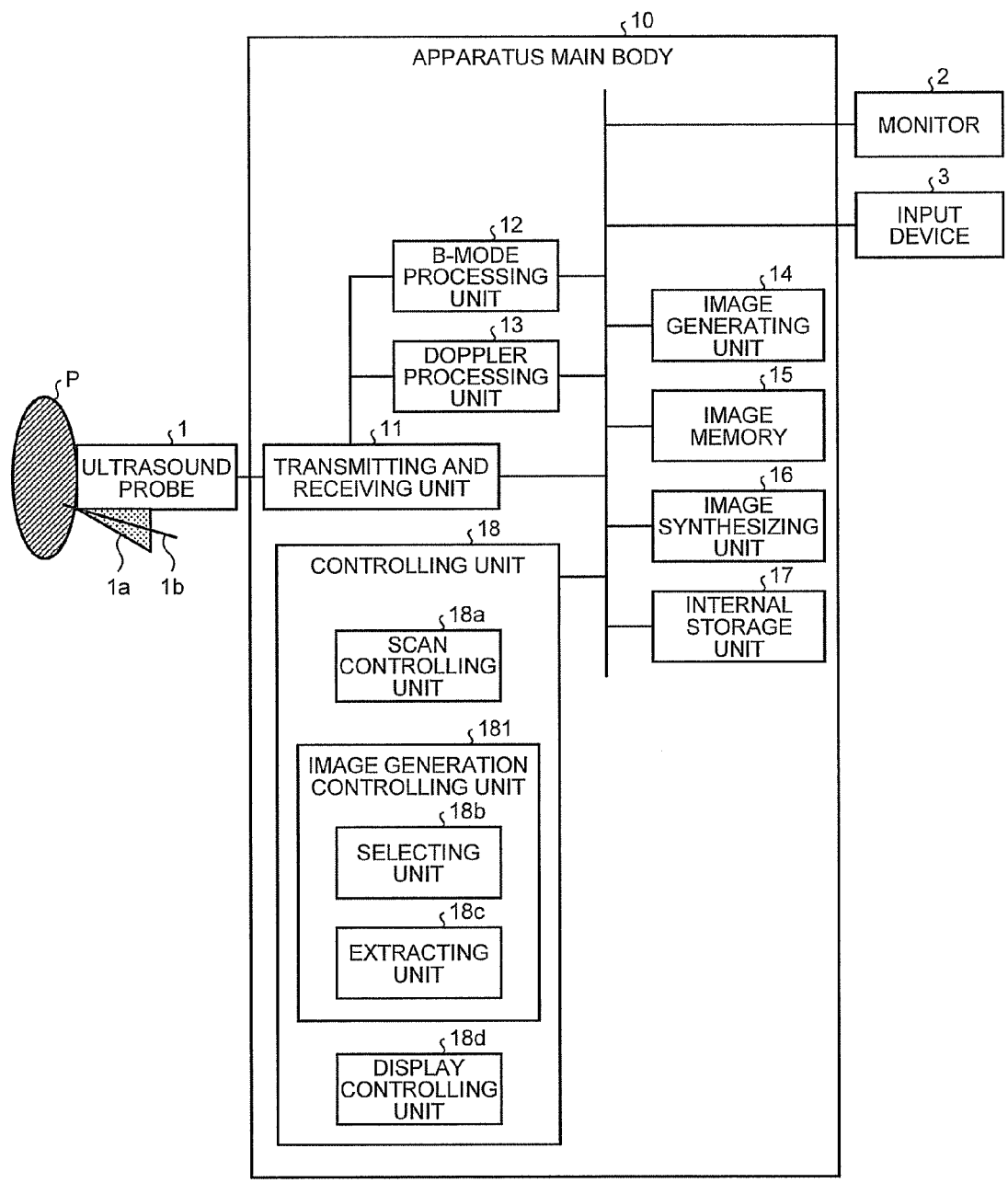
FIG. 1 is a diagram for explaining a configuration of an ultrasound diagnosis apparatus according to a first embodiment.

First, a configuration of an ultrasound diagnosis apparatus according to a first embodiment will be explained. FIG. 1 is a diagram for explaining the configuration of the ultrasound diagnosis apparatus according to the first embodiment. As shown in FIG. 1, the ultrasound diagnosis apparatus according to the first embodiment includes an ultrasound probe 1, a monitor 2, an input device 3, and an apparatus main body 10.

The ultrasound probe 1 is detachably connected to the apparatus main body 10. The ultrasound probe 1 includes a plurality of piezoelectric vibrators, which generate an ultrasound wave based on a drive signal supplied from a transmitting and receiving unit 11 included in the apparatus main body 10 (explained later). Further, the ultrasound probe 1 receives a reflected wave from an examined subject P and converts the received reflected wave into an electric signal. Further, the ultrasound probe 1 includes matching layers included in the piezoelectric vibrators, as well as a backing member that prevents ultrasound waves from propagating rearward from the piezoelectric vibrators.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected-wave signal by the plurality of piezoelectric vibrators included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift, depending on a velocity component of the moving members with respect to the ultrasound wave transmission direction (hereinafter, "ultrasound transmission direction").

The first embodiment is applicable to a situation where the ultrasound probe 1 shown in FIG. 1 is configured with a one-dimensional ultrasound probe in which the plurality of piezoelectric vibrators are arranged in a row, to a situation where the ultrasound probe 1 is configured with a one-dimensional ultrasound probe in which the plurality of piezoelectric vibrators arranged in a row are mechanically oscillated, and to a situation where the ultrasound probe 1 is configured with a two-dimensional ultrasound probe in which the plurality of piezoelectric vibrators are arranged two-dimensionally in a matrix formation.

Further, a puncture adapter 1a is attached to the ultrasound probe 1 according to the first embodiment so that a medical doctor is able to perform a puncture process for, for example, performing a test on a tissue in the subject's body or providing a radio frequency ablation treatment, while referring to an ultrasound image. Further, a puncture needle 1b is attached to the puncture adapter 1a. While referring to the ultrasound image, the medical doctor inserts the puncture needle 1b attached to the puncture adapter 1a to reach a target site of the subject P.

The input device 3 includes a mouse, a keyboard, a button, a panel switch, a touch command screen, a foot switch, a trackball, and the like. The input device 3 receives various types of setting requests from an operator of the ultrasound diagnosis apparatus and transfers the received various types of setting requests to the apparatus main body 10. For example, when the operator presses an end button or a freeze button included in the input device 3, the transmission and reception of the ultrasound wave is ended so that the ultrasound diagnosis apparatus according to the first embodiment goes into a temporarily-halted state. In addition, the operator is able to set and change, via the input device 3, oblique angles used in ultrasound transmissions for performing a second scanning process (an oblique scanning process), which is explained later.

The monitor 2 displays a Graphical User Interface (GUI) used by the operator of the ultrasound diagnosis apparatus to input the various types of setting requests through the input device 3 and displays an ultrasound image generated by the apparatus main body 10.

The apparatus main body 10 is an apparatus that generates the ultrasound image based on the reflected wave received by the ultrasound probe 1. As shown in FIG. 1, the apparatus main body 10 includes the transmitting and receiving unit 11, a B-mode processing unit 12, a Doppler processing unit 13, an image generating unit 14, an image memory 15, an image synthesizing unit 16, an internal storage unit 17, and a controlling unit 18.

The transmitting and receiving unit 11 includes a trigger generating circuit, a delaying circuit, a pulser circuit, and the like and supplies the drive signal to the ultrasound probe 1. The pulser circuit repeatedly generates a rate pulse for forming a transmission ultrasound wave at a predetermined rate frequency. Further, the delaying circuit applies a delay period that is required to converge the ultrasound wave generated by the ultrasound probe 1 into the form of a beam and to determine transmission directionality and that corresponds to each of the piezoelectric vibrators, to each of the rate pulses generated by the pulser circuit. Further, the trigger generating circuit applies a drive signal (a drive pulse) to the ultrasound probe 1 with timing based on the rate pulses. In other words, the delaying circuit arbitrarily adjusts the directions of the transmissions from the piezoelectric vibrator surfaces, by varying the delay periods applied to the rate pulses.

The transmitting and receiving unit 11 has a function to be able to instantly change the transmission frequency, the transmission drive voltage, and the like, for the purpose of executing a predetermined scanning sequence based on an instruction from the controlling unit 18 (explained later). In particular, the configuration to change the transmission drive voltage is realized by using a linear-amplifier-type transmitting circuit of which the value can be instantly switched or by using a mechanism configured to electrically switch between a plurality of power source units.

Further, the transmitting and receiving unit 11 includes an amplifier circuit, an Analog/Digital (A/D) converter, an adder, and the like and generates reflected-wave data by performing various types of processes on the reflected-wave signal received by the ultrasound probe 1. The amplifier circuit amplifies the reflected-wave signal for each of channels and performs a gain correcting process thereon. The A/D converter applies an A/D conversion to the gain-corrected reflected-wave signal and further applies thereto a delay period required to determine reception directionality. The adder generates the reflected-wave data by performing an adding process on reflected-wave signals, based on the applied delay periods. As a result of the adding process performed by the adder, reflected components from the direction corresponding to the reception directionality of the reflected-wave signal are emphasized.

In this manner, the transmitting and receiving unit 11 controls the transmission directionality and the reception directionality in the transmission and the reception of the ultrasound wave. The transmitting and receiving unit 11 has a function to be able to instantly change delay information, the transmission frequency, the transmission drive voltage, the number of aperture elements, and the like, under the control of the controlling unit 18 (explained later). Further, the transmitting and receiving unit 11 is also able to transmit and receive a waveform that is different for each of the frames or for each of the rates.

The B-mode processing unit 12 receives the reflected-wave data from the transmitting and receiving unit 11 and generates data (B-mode data) in which the strength of each signal is expressed by a degree of brightness, by performing a logarithmic amplification, an envelope detection process, and the like on the received reflected-wave data.

The Doppler processing unit 13 receives the reflected-wave data from the transmitting and receiving unit 11, extracts bloodstreams, tissues, and contrast echo components under the influence of the Doppler effect by performing a frequency analysis so as to obtain velocity information from the received reflected-wave data, and further generates data (Doppler data) obtained by extracting moving member information such as an average velocity, the dispersion, the power, and the like for a plurality of points. The data generated by the B-mode processing unit 12 and the Doppler processing unit 13 may be referred to as raw data.

The image generating unit 14 generates an ultrasound image from the data generated by the B-mode processing unit 12 and the Doppler processing unit 13. More specifically, from the B-mode data generated by the B-mode processing unit 12, the image generating unit 14 generates the B-mode image in which the strength of the reflected wave is expressed by a degree of brightness. Further, from the Doppler data generated by the Doppler processing unit 13, the image generating unit 14 generates an average velocity image, a dispersion image, and a power image, expressing the moving member information, or a color Doppler image, which is an image combining these images.

Further, the image generating unit 14 is also able to generate a synthesized image by synthesizing text information of various parameters, scale graduations, body marks, and the like with an ultrasound image.

In this situation, the image generating unit 14 converts (by performing a scan convert process) a scanning line signal sequence from an ultrasound scan into a scanning line signal sequence in a video format used by, for example, television and generates the ultrasound image serving as a displayed image. Further, as various types of image processing processes other than the scan convert process, the image generating unit 14 performs, for example, an image processing process (a smoothing process) to re-generate a brightness average-value image while using a plurality of image frames resulting from the scan convert process and an image processing process (an edge emphasizing process) by employing a differential filter within an image.

Further, the image generating unit 14 has installed therein a storage memory for storing therein image data and is able to perform a process of reconstructing a three-dimensional image. Further, after a diagnosis is made, the operator is able to acquire, for example, an image recorded during a medical examination, out of the storage memory installed in the image generating unit 14.

The image synthesizing unit 16 synthesizes text information of various parameters, scale graduations, body marks, and the like with the ultrasound image generated by the image generating unit 14 and outputs the result to the monitor 2 as a video signal. In the first embodiment, the image synthesizing unit 16 generates a synthesized image obtained by synthesizing together a subject-body image and a needle image. The synthesized image generated by the image synthesizing unit 16 according to the first embodiment will be explained in detail later.

The image memory 15 is a memory for storing therein the ultrasound image generated by the image generating unit 14 and the synthesized image generated by the image synthesizing unit 16. For example, the image memory 15 stores therein ultrasound images corresponding to a plurality of frames immediately prior to pressing of the freeze button. The ultrasound diagnosis apparatus is also able to display ultrasound moving images by successively displaying (called "cine display") the images stored in the image memory 15.

The internal storage unit 17 stores therein various types of data such as a control computer program (hereinafter, "control program") to realize ultrasound transmissions and receptions, image processing, and display processing, as well as diagnosis information (e.g., patients' IDs, medical doctors' observations), diagnosis protocols, and various types of body marks. Further, the internal storage unit 17 may be used, as necessary, for storing therein any of the images stored in the image memory 15. Furthermore, the data stored in the internal storage unit 17 may be transferred to any external peripheral device via an interface circuit (not shown).

Further, the internal storage unit 17 according to the first embodiment stores therein the angle at which the puncture needle 1b is attached to the puncture adapter 1a, as a puncture angle of the puncture needle 1b. For example, when the puncture adapter 1a is attached, the internal storage unit 17 stores therein an attachment angle "A" of the puncture adapter 1a, as an insertion angle "A" of the puncture needle 1b.

The controlling unit 18 controls the entire processes performed by the ultrasound diagnosis apparatus. More specifically, based on the various types of setting requests input by the operator via the input device 3 and various types of control programs and various types of data read from the internal storage unit 17, the controlling unit 18 controls processes performed by the transmitting and receiving unit 11, the B-mode processing unit 12, the Doppler processing unit 13, the image generating unit 14, and the image synthesizing unit 16. For example, a scan controlling unit 18a shown in FIG. 1 controls an ultrasound scanning process performed by the ultrasound probe 1, via the transmitting and receiving unit 11. Further, a display controlling unit 18d shown in FIG. 1 exercises control so that the ultrasound images and the synthesized images stored in the image memory 15 are displayed on the monitor 2.

In addition to the scan controlling unit 18a and the display controlling unit 18d, the controlling unit 18 according to the first embodiment also includes an image generation controlling unit 181, as shown in FIG. 1. As shown in FIG. 1, the image generation controlling unit 181 includes a selecting unit 18b and an extracting unit 18c. The processes performed by the scan controlling unit 18a, the selecting unit 18b, the extracting unit 18c, and the display controlling unit 18d in the first embodiment will be explained in detail later.

An overall configuration of the ultrasound diagnosis apparatus according to the first embodiment has thus been explained. The ultrasound diagnosis apparatus according to the first embodiment configured as described above generates an ultrasound image (a B-mode image) by taking an image of a tissue in the body of the subject P into whom the puncture needle 1b has been inserted. Further, the ultrasound diagnosis apparatus according to the first embodiment generates an ultrasound image in which visibility of both the tissue in the subject's body and the puncture needle is improved, as a result of controlling processes performed by the controlling unit 18, which are explained in detail below. For example, when the operator presses a puncture mode start button included in the input device 3, the ultrasound diagnosis apparatus according to the first embodiment starts the process described below. As another example, when the operator presses a puncture mode end button included in the input device 3, the ultrasound diagnosis apparatus according to the first embodiment ends the process described below.

First, when performing an ultrasound scanning process on the subject P into whom the puncture needle 1b has been inserted, the scan controlling unit 18a causes the ultrasound probe 1 to perform a first scanning process by transmitting an ultrasound wave in a first direction with respect to the surface of the vibrators for the purpose of taking an image of the tissue of the subject P and a second scanning process by transmitting an ultrasound wave in each of a plurality of directions with respect to the surface of the vibrators. The first scanning process is an ultrasound scanning process performed by transmitting the ultrasound wave in the first direction that is optimal for taking the image of the tissue of the subject P, along an alignment direction of the vibrators. More specifically, the first direction is a direction perpendicular to the surface of the vibrators of the ultrasound probe 1. For example, the first direction is a direction perpendicular to a lateral direction. As long as the first direction is an ultrasound transmission direction that is optimal for taking the image of the tissue of the subject P, the first direction may be a direction other than the direction perpendicular to the surface of the vibrators.

Figure 2:
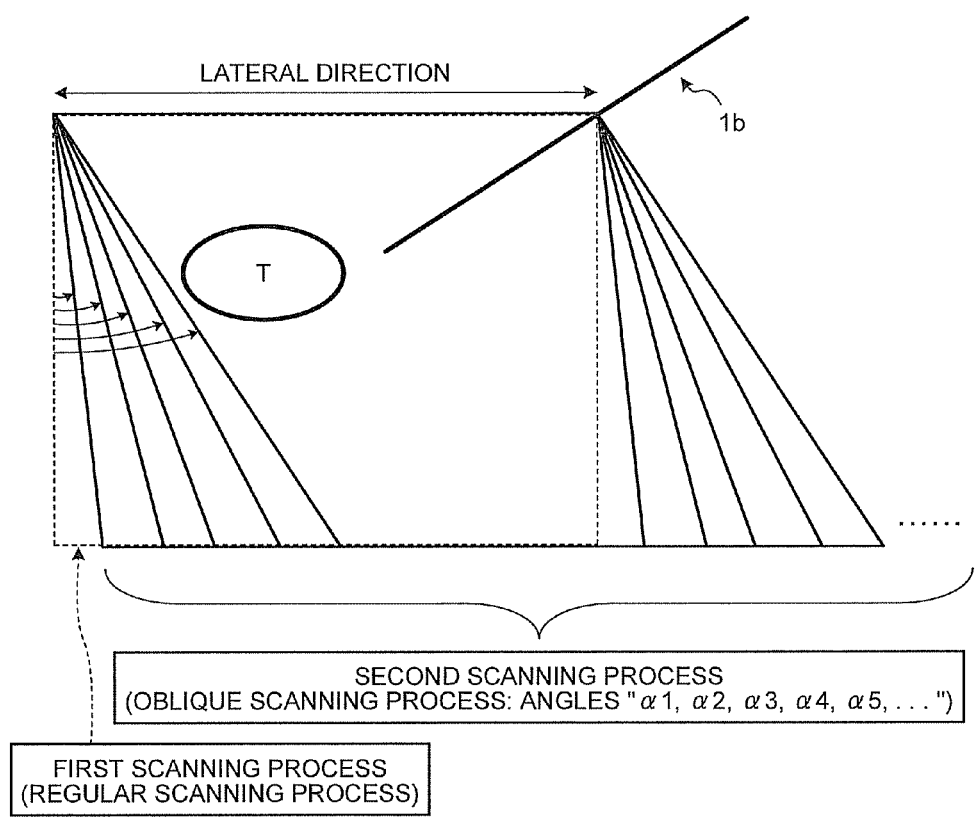
FIG. 2 is a drawing for explaining a scan controlling unit according to the first embodiment.

In contrast, the second scanning process is an ultrasound scanning process performed by transmitting an ultrasound wave in each of the plurality of directions, for the purpose of searching for an ultrasound transmission direction that is optimal for taking an image of the puncture needle 1b inserted into the subject P. During the second scanning process, an ultrasound wave is transmitted in each of the plurality of directions, along the alignment direction of the vibrators. More specifically, each of the plurality of directions is a direction other than the direction perpendicular to the surface of the vibrators of the ultrasound probe 1. For example, each of the plurality of directions is a direction other than the direction perpendicular to the lateral direction. The ultrasound transmission directions used during the second scanning process may include the first direction. FIG. 2 is a drawing for explaining the scan controlling unit according to the first embodiment.

In the example shown in FIG. 2, the puncture needle 1b in inserted for a target site (T). In this situation, as the first scanning process, the scan controlling unit 18a causes an ultrasound transmission to be performed in the direction perpendicular to the lateral direction as shown in FIG. 2, in the same manner as in a regular scanning process that is generally performed to generate a B-mode image. Further, as shown in FIG. 2, the scan controlling unit 18a causes oblique scanning processes to be performed at a plurality of angles "$\alpha 1, \alpha 2, \alpha 3, \alpha 4, \alpha 5, \ldots$", as the second scanning process.

In this situation, the scan controlling unit 18a causes the second scanning process to be performed by obtaining the insertion angle "A" of the puncture needle 1b from the internal storage unit 17 and setting a plurality of oblique scan angles in the vicinity of the direction perpendicular to a puncture line that is set based on the insertion angle "A". For example, the scan controlling unit 18a calculates an angle "B" forming the direction perpendicular to the puncture line. Further, the scan controlling unit 18a determines that the second scanning process should be performed in the range from the angle "$B-B_0$" to the angle "$B-B_1$" at intervals of an angle "$\beta$". In this situation, the angles "$B_0, B_1$, and $\beta$" are set by the operator or an administrator of the ultrasound diagnosis apparatus. Further, it is possible for the operator to arbitrarily change any of the angles "$B_0, B_1$, and $\beta$". It is acceptable if the intervals at which the oblique scanning process is performed are equal to one another. Alternatively, it is acceptable to vary the intervals in such a manner that the interval is "$\beta 1$" in an area positioned close to the angle "B", whereas the interval is "$\beta 2$ (where $\mu 2 > \beta 1$)" in an area positioned distant from the angle "B".

The method for obtaining the puncture angle is not limited to the example described above. For example, it is acceptable to obtain the puncture angle, based on a detection result of a position sensor. Examples of the position sensor include a magnetic sensor. For example, the magnetic sensor is attached to the puncture needle 1b, and a magnetic field generating coil is placed in a predetermined position. Further, the magnetic sensor detects a magnetic signal generated by the magnetic field generating coil. Based on a detection result of the magnetic sensor, the scan controlling unit 18a calculates a coordinate position of the magnetic sensor with respect to the magnetic field generating coil. After that, the scan controlling unit 18a obtains the puncture angle by calculating the angle between the surface of the ultrasound probe 1 and the puncture needle 1b, based on the coordinate position of the magnetic sensor.

When it is not possible to obtain the puncture angle by using the attachment angle of the puncture adapter 1a or a position sensor, e.g., when the puncture process is performed in a free-hand manner without using the adapter or a sensor function, the scan controlling unit 18a causes the second scanning process to be performed at angular intervals that are set in advance.

Figure 3:
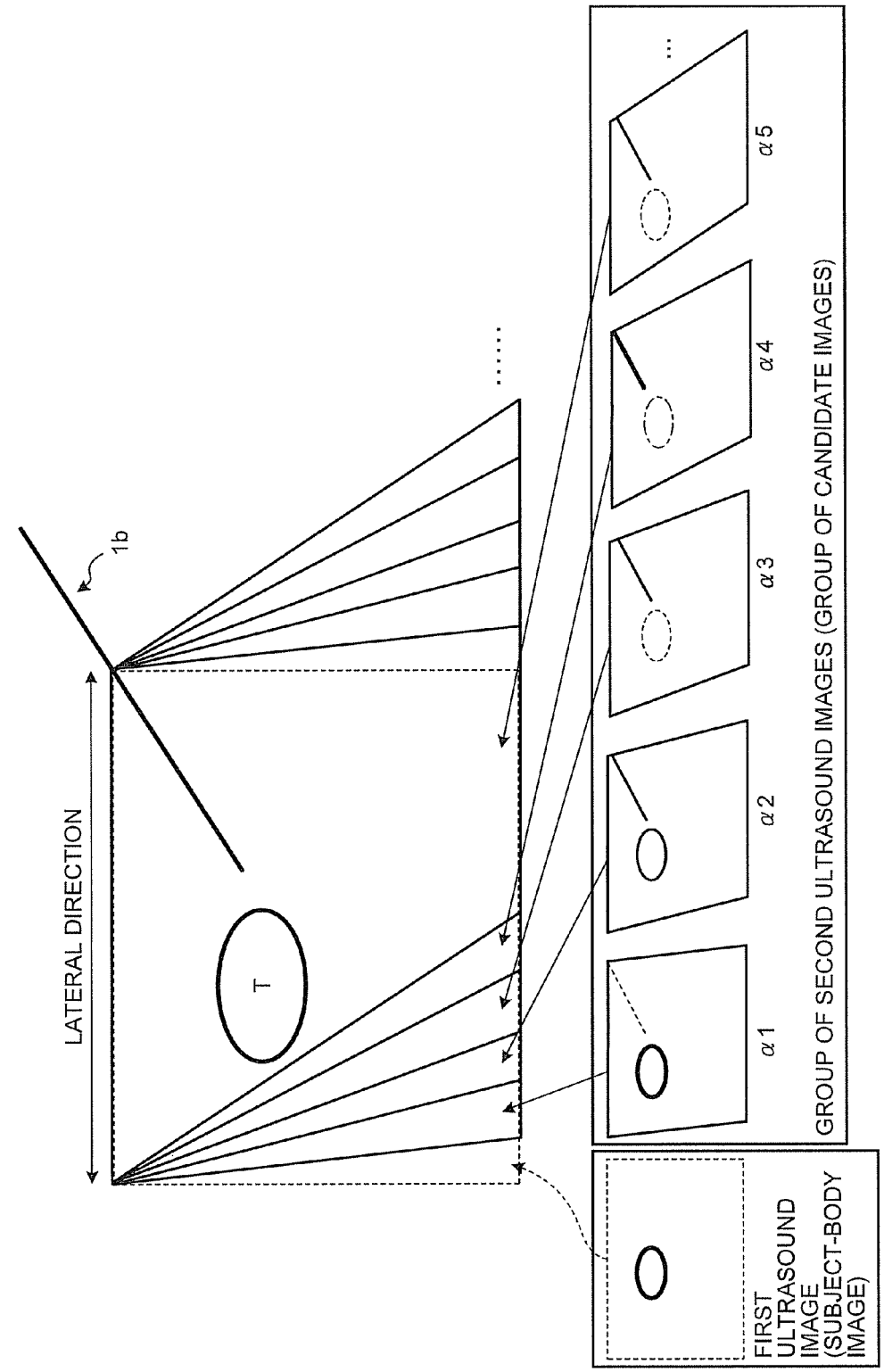
FIG. 3 is a drawing for explaining an image generating unit according to the first embodiment.

Further, the image generating unit 14 shown in FIG. 1 generates a first ultrasound image by using a reflected wave received by the ultrasound probe 1 during the first scanning process. Further, the image generating unit 14 generates a group of second ultrasound images that are ultrasound images corresponding to the plurality of directions by using reflected waves received by the ultrasound probe during the second scanning process. FIG. 3 is a drawing for explaining the image generating unit according to the first embodiment.

More specifically, as shown in FIG. 3, the image generating unit 14 generates the first ultrasound image as a subject-body image in which the visibility of the tissue in the subject's body is not degraded by artifacts, by using the B-mode data generated by performing the first scanning process (the regular scanning process).

Further, as shown in FIG. 3, the image generating unit 14 generates the group of second ultrasound images that are the ultrasound images corresponding to the angles "$\alpha 1, \alpha 2, \alpha 3, \alpha 4, \alpha 5, \ldots$", by using a group of pieces of B-mode data corresponding to the angles "$\alpha 1, \alpha 2, \alpha 3, \alpha 4, \alpha 5, \ldots$" generated by performing the second scanning process (the oblique scanning processes). The group of second ultrasound images serves as a group of candidate images used for generating a needle image in which the visibility of the puncture needle is improved.

Returning to the description of FIG. 1, the image generation controlling unit 181 controls the image generating unit 14 so as to generate the needle image in which the puncture needle 1b is rendered with a high level of brightness, based on an analysis result obtained by analyzing the brightness distribution of each member of the group of second ultrasound images. The selecting unit 18b included in the image generation controlling unit 181 has a function of analyzing the brightness distribution within each image. Out of the analyzed group of images, the selecting unit 18b selects an image of which the analysis result satisfies a predetermined condition, as a third ultrasound image in which the puncture needle 1b is rendered with a high level of brightness. In the first embodiment, the selecting unit 18b selects the third ultrasound image in which the puncture needle 1b is rendered with a high level of brightness, out of the group of second ultrasound images generated by the image generating unit 14, based on the brightness distribution of each of the ultrasound images. In other words, the selecting unit 18b determines the oblique angle with which the puncture needle 1b is rendered with the high level of brightness. In the following sections, the predetermined condition used for selecting the third ultrasound image according to the first embodiment will be explained.

For example, the selecting unit 18b extracts a brightness level of each of the pixels in each of the images generated as the group of second ultrasound images and generates a histogram (a brightness curve) indicating a brightness distribution. In this situation, because the puncture needle 1b is a highly reflective member, a B-mode image generated by transmitting an ultrasound wave in a direction substantially perpendicular to the puncture needle 1b has high frequency of appearance of pixels each having a high level of brightness. Accordingly, the selecting unit 18b determines an image having the maximum frequency of appearance of brightness levels that are equal to or higher than a predetermined threshold value, based on the histogram of each of the pixels.

When, however, an ultrasound scanning process is performed at an angle substantially perpendicular to the puncture needle 1b, a multiple reflection artifact occurs in a B-mode image.

To cope with this situation, the selecting unit 18b selects, out of the group of second ultrasound images, an image generated from the reflected wave received in such an ultrasound transmission performed at the angle closest to the ultrasound transmission direction used for receiving the reflected wave from which the image having the maximum frequency of appearance of pixels each having a brightness level equal to or higher than the predetermined threshold value was generated, as the third ultrasound image. In other words, the selecting unit 18b selects, a frame immediately before or immediately after the frame in which pixels having high levels of brightness appear with high frequency, as the third ultrasound image.

For example, the selecting unit 18b determines the ultrasound image corresponding to the angle "α4" shown in FIG. 3, as the image having the maximum frequency of appearance of pixels each having a brightness level equal to or higher than the predetermined threshold value. Further, the selecting unit 18b selects the ultrasound image corresponding to the angle "α3" shown in FIG. 3, as the third ultrasound image. In other words, the selecting unit 18b determines the angle "α3" to be the oblique angle with which the puncture needle 1b is rendered with the high level of brightness.

Figure 4:
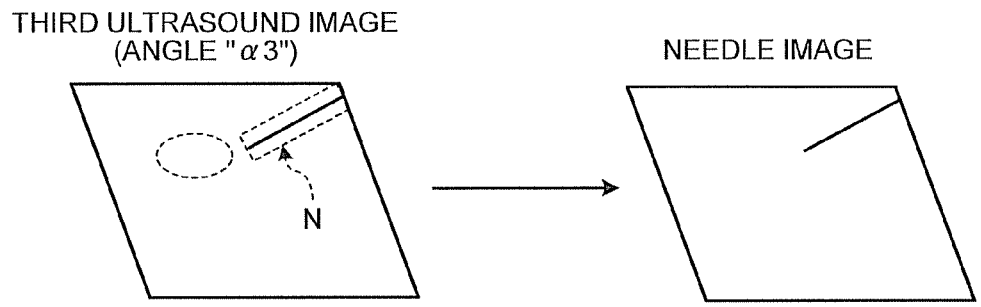
FIG. 4 is a drawing for explaining an extracting unit according to the first embodiment.

Returning to the description of FIG. 1, the extracting unit 18c included in the image generation controlling unit 181 extracts a high brightness area in the third ultrasound image selected by the selecting unit 18b, as a puncture needle area. Further, the extracting unit 18c controls the image generating unit 14 so as to generate a needle image by using the extracted puncture needle area. FIG. 4 is a drawing for explaining the extracting unit according to the first embodiment.

For example, the operator sets an extraction-purpose threshold value used for extracting the high brightness area, in advance. Further, as shown in FIG. 4, the extracting unit 18c extracts a high brightness area N having brightness levels equal to or higher than the extraction-purpose threshold value within the third ultrasound image (the angle "α3"), as the puncture needle area. Further, the extracting unit 18c notifies the image generating unit 14 of the coordinates of the high brightness area N within the third ultrasound image. While using the notified coordinates, the image generating unit 14 generates the needle image shown in FIG. 4 by, for example, replacing the brightness levels with "0" in the area other than the high brightness area N within the third ultrasound image.

Alternatively, another arrangement is acceptable in which the extracting unit 18c extracts, out of the third ultrasound image, a straight-line area in which a high brightness area substantially forms a straight line, as the puncture needle area. For example, the extracting unit 18c extracts a straight line by applying a straight-line extraction method such as a Hough transform to the third ultrasound image (the angle "α3"). Further, the extracting unit 18c notifies the image generating unit 14 of the coordinates of the extracted straight line. The image generating unit 14 then generates the needle image by using the notified coordinates. In this situation, the operator determines whether the extracting unit 18c performs the extracting process using the extraction-purpose threshold value or performs the extracting process using the straight-line extraction method.

Figure 5:
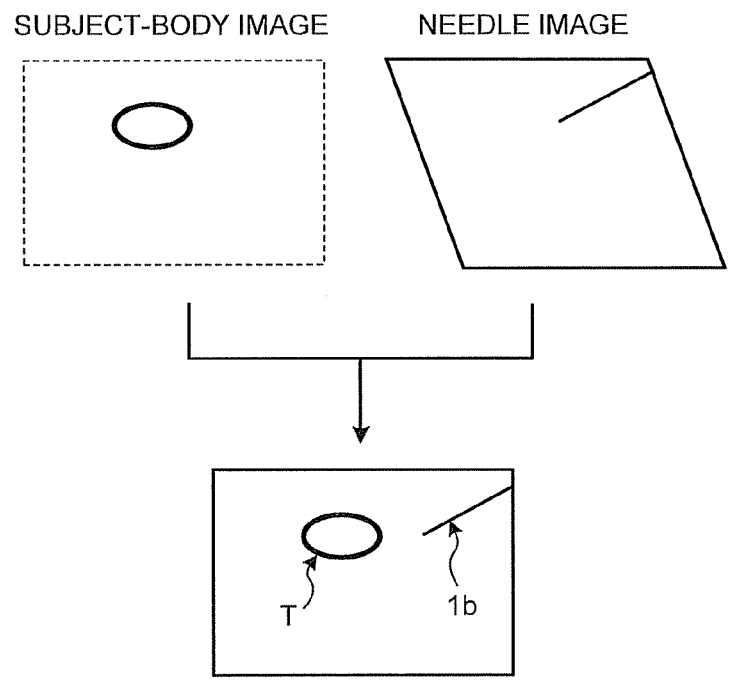
FIG. 5 is a drawing for explaining an image synthesizing unit according to the first embodiment.

Returning to the description of FIG. 1, as shown in FIG. 5, the image synthesizing unit 16 generates a synthesized image by synthesizing together the first ultrasound image (the subject-body image) and the needle image generated by the image generating unit 14. FIG. 5 is a drawing for explaining the image synthesizing unit according to the first embodiment. In the synthesized image shown in FIG. 5, the target site T and the puncture needle 1b are both rendered clearly.

Returning to the description of FIG. 1, the display controlling unit 18d exercises control so that the synthesized image generated by the image synthesizing unit 16 is displayed on the monitor 2.

Figure 6:
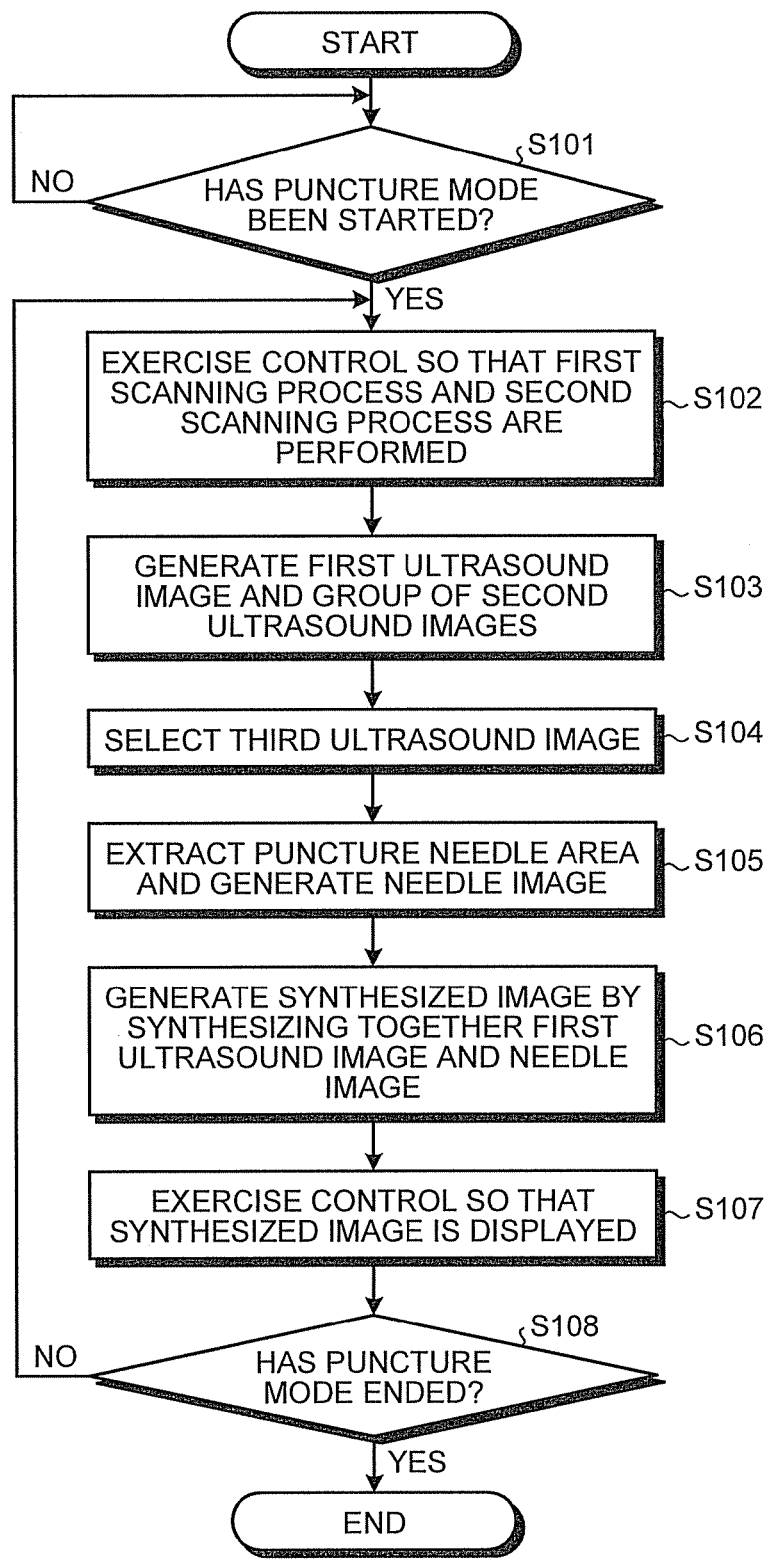
FIG. 6 is a flowchart for explaining a process performed by the ultrasound diagnosis apparatus according to the first embodiment.

Next, a process performed by the ultrasound diagnosis apparatus according to the first embodiment will be explained, with reference to FIG. 6. FIG. 6 is a flowchart for explaining the process performed by the ultrasound diagnosis apparatus according to the first embodiment.

As shown in FIG. 6, the ultrasound diagnosis apparatus according to the first embodiment judges whether a puncture mode has been started (step S101). In this situation, if the puncture mode has not been started (step S101: No), the ultrasound diagnosis apparatus according to the first embodiment is in a standby state until the puncture mode is started.

On the contrary, if the puncture mode has been started (step S101: Yes), the scan controlling unit 18a controls the ultrasound probe 1 so as to perform the first scanning process and the second scanning process (step S102).

After that, the image generating unit 14 generates a first ultrasound image (a subject-body image) and a group of second ultrasound images (a group of candidate images) (step S103), so that the selecting unit 18b selects a third ultrasound image out of the group of second ultrasound images (step S104). More specifically, the selecting unit 18b determines the image having the maximum frequency of appearance of pixels each having a brightness level equal to or higher than the predetermined threshold value, out of the group of second ultrasound images. Subsequently, the selecting unit 18b selects an image generated from the reflected wave received in such an ultrasound transmission performed at the angle closest to the ultrasound transmission direction used for receiving the reflected wave from which the determined image was generated, as the third ultrasound image.

After that, the extracting unit 18c extracts a puncture needle area from the third ultrasound image, so that the image generating unit 14 generates a needle image based on the puncture needle area extracted by the extracting unit 18c (step S105). Subsequently, the image synthesizing unit 16 generates a synthesized image by synthesizing together the first ultrasound image and the needle image (step S106). As a result, a synthesized image corresponding to one frame has been generated.

Further, the display controlling unit 18d exercises control so that the synthesized image is displayed on the monitor 2 (step S107), and it is then judged whether the puncture mode has ended (step S108). In this situation, if the puncture mode has not ended (step S108: No), the ultrasound diagnosis apparatus returns to step S102 and exercises control so that a scanning process is performed so as to generate a synthesized image corresponding to the next frame.

On the contrary, if the puncture mode has ended (step S108: Yes), the ultrasound diagnosis apparatus ends the process. Another arrangement is acceptable in which the display controlling unit 18d exercises control so that any of the first ultrasound image, the third ultrasound image, and the group of second ultrasound images is displayed together with the synthesized image, while positioned next to each other. Also, in the example described above, the judgment of whether the puncture mode has ended is made after the synthesized image is displayed at step S107; however, it is acceptable to configure the first embodiment so that the judgment of whether the puncture mode has ended is made after the first scanning process and the second scanning process are performed at step S102. In other words, the arrangement is acceptable in which the first scanning process and the second scanning process are sequentially performed in parallel with the processes at steps S103 through S107.

As explained above, in the first embodiment, when performing the ultrasound scanning process on the subject P into whom the puncture needle 1b has been inserted, the scan controlling unit 18a causes the ultrasound probe 1 to perform the first scanning process by, for example, transmitting the ultrasound wave in the direction perpendicular to the lateral direction, as well as the second scanning process by, for example, transmitting the ultrasound wave in each of the plurality of directions other than the direction perpendicular to the lateral direction. Further, the image generating unit 14 generates the first ultrasound image by using the reflected wave received by the ultrasound probe 1 during the first scanning process and generates the group of second ultrasound images that are the ultrasound images corresponding to the plurality of directions by using the reflected waves received by the ultrasound probe 1 during the second scanning process.

After that, the selecting unit 18b selects the third ultrasound image in which the puncture needle 1b is rendered with the high level of brightness, out of the group of second ultrasound images generated by the image generating unit 14, based on the brightness distribution of each of the ultrasound images. Further, the extracting unit 18c extracts the high brightness area within the third ultrasound image selected by the selecting unit 18b as the puncture needle area, whereas the image generating unit 14 is controlled so as to generate the needle image by using the extracted puncture needle area. After that, the image synthesizing unit 16 generates the synthesized image by synthesizing together the first ultrasound image and the needle image generated by the image generating unit 14. The display controlling unit 18d exercises control so that the synthesized image generated by the image synthesizing unit 16 is displayed on the monitor 2.

As explained above, according to the first embodiment, the first ultrasound image, which is the subject-body image, is generated by performing the first scanning process that is optimal for observing the tissue in the subject's body. Further, according to the first embodiment, the oblique angle that is optimal for observing the puncture needle 1b is selected. Further, according to the first embodiment, the needle image is generated after extracting the area corresponding to the puncture needle 1b, from the third ultrasound image generated by performing the oblique scanning process at the selected angle. In other words, the needle image generated in the first embodiment does not contain tissues in the subject's body that are rendered unclearly due to the side-lobe effect, unlike in the conventional example. Accordingly, according to the first embodiment, it is possible to improve the visibility of both the tissue in the subject's body and the puncture needle. Further, according to the first embodiment, because it is possible to display the synthesized image in which the visibility of both the tissue in the subject's body and the puncture needle is improved, it is possible to enhance safety and the precision level of the puncture process and thus to aid the operator who performs the puncture process.

In addition, according to the first embodiment, the selecting unit 18b determines the ultrasound transmission direction used for receiving the reflected wave from which the image having the maximum frequency of appearance of pixels each having a brightness level equal to or higher than the predetermined threshold value was generated, from among the group of second ultrasound images. Further, the selecting unit 18b selects the image generated from the reflected wave received in such an ultrasound transmission performed at the angle closest to the determined ultrasound transmission direction, as the third ultrasound image.

In other words, an ultrasound image generated by performing an oblique scanning process at the angle exactly perpendicular to the insertion direction of the puncture needle 1b has a high possibility of containing a multiple reflection artifact. Thus, even if a high brightness area is extracted from such an ultrasound image, the needle image also has a possibility of containing an artifact related to the puncture needle 1b. In contrast, the third ultrasound image selected as a result of the process described above has a lower possibility of containing a multiple reflection artifact. Accordingly, the first embodiment is able to provide the needle image having fewer artifacts.

In addition, in the first embodiment, according to a setting made by the operator, for example, the extracting unit 18c extracts the straight-line area in which the high brightness area substantially forms a straight line, from the third ultrasound image, as the puncture needle area. In other words, in the first embodiment, only the straight-line part corresponding to the shape of the puncture needle 1b is generated as the needle image. As a result, the first embodiment is able to provide the needle image in which only the part corresponding to the puncture needle 1b is rendered.

Figure 7:
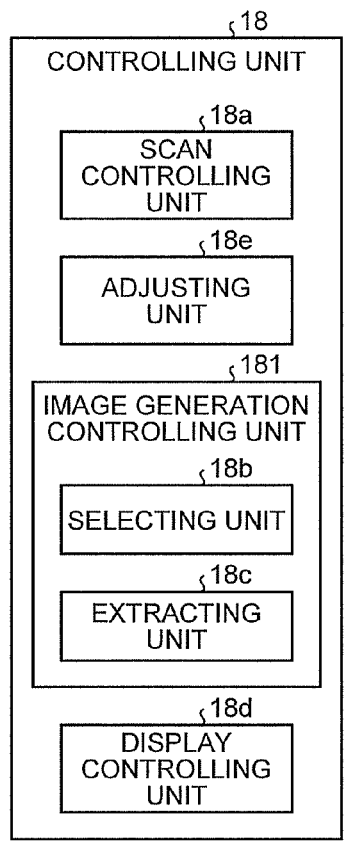
FIG. 7 is a diagram for explaining a configuration of a controlling unit according to a second embodiment.

In a second embodiment, an example will be explained in which a process to select a third ultrasound image is performed after a brightness adjusting process is performed on the group of second ultrasound images, with reference to FIG. 7 and so on. FIG. 7 is a diagram for explaining a configuration of a controlling unit according to the second embodiment.

As shown in FIG. 7, the controlling unit 18 according to the second embodiment is different from the controlling unit 18 according to the first embodiment shown in FIG. 1, for further including an adjusting unit 18e. In the following sections, the second embodiment will be explained while a focus is placed on the difference. In the second embodiment also, like in the first embodiment, the first ultrasound image and the group of second ultrasound images are generated after the first scanning process and the second scanning process are performed.

When an ultrasound beam is arranged to be oblique, the brightness levels of the entire image become higher and the image quality becomes degraded, due to the side-lobe effect. For this reason, it is desirable to perform a process to make the brightness levels of the entire image uniform, on the group of images from which the third ultrasound image is selected, so that the brightness levels of the entire image are not dependent on the oblique scan angle.

For this reason, in the second embodiment, the adjusting unit 18e generates a group of third ultrasound images in which the brightness levels of the entirety of each of the ultrasound images are substantially uniform, by performing a brightness adjusting process on the group of second ultrasound images generated by the image generating unit 14.

Figure 8:
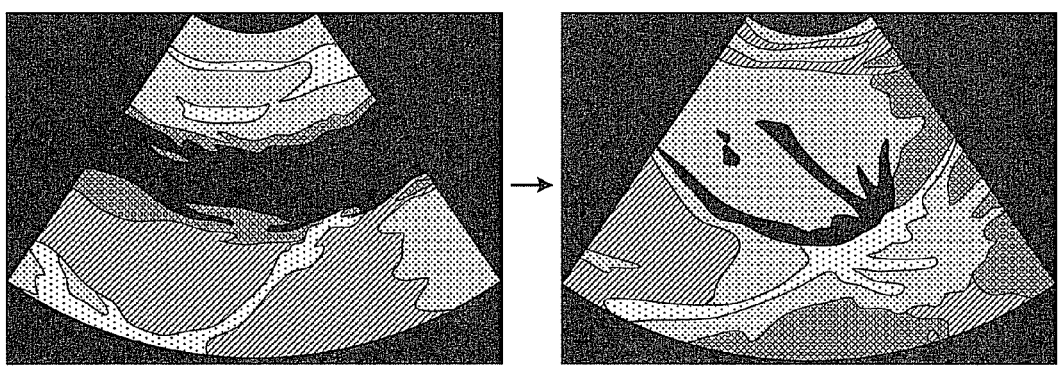
FIG. 8 is a drawing for explaining an adjusting unit according to the second embodiment.

In one example, the adjusting unit 18e divides each member of the group of pieces of raw data (the group of pieces of B-mode data) corresponding to the group of second ultrasound images, into a plurality of sections. Further, the adjusting unit 18e determines whether the signal in each of the sections is a subject-body signal or a noise signal. Further, the adjusting unit 18e calculates a gain curve so as to reduce the brightness levels if the signal is a noise signal and so as to make the brightness levels spatially uniform if the signal is a subject-body signal. Further, the adjusting unit 18e generates the group of third ultrasound images from the group of pieces of raw data corresponding to the group of second ultrasound images, by using the calculated gain curve. FIG. 8 is a drawing for explaining the adjusting unit according to the second embodiment.

As a result of the process described above, the adjusting unit 18e generates, as shown in FIG. 8, the ultrasound images (the group of third ultrasound images) in which the noise is suppressed and the brightness levels of the subject-body signals are adjusted. Alternatively, another arrangement is acceptable in which the adjusting unit 18e notifies the image generating unit 14 of the calculated gain curve and exercises control so that the image generating unit 14 generates the group of third ultrasound images.

Further, while using the group of third ultrasound images as a group of candidate images, the selecting unit 18b included in the image generation controlling unit 181 according to the second embodiment selects a third ultrasound image out of the group of third ultrasound images. In other words, the selecting unit 18b selects the third ultrasound image out of the group of third ultrasound images, by using a histogram (a brightness curve) indicating the brightness distribution of each member of the group of third ultrasound images generated from the second ultrasound images, instead of selecting out of the group of second ultrasound images. In the following sections, a predetermined condition used for selecting the third ultrasound image according to the second embodiment will be explained.

More specifically, by referring to the histogram of each member of the group of third ultrasound images, the selecting unit 18b determines the image having the maximum frequency of appearance of brightness levels that are equal to or higher than the predetermined threshold value and further selects the image generated from the reflected wave received in such an ultrasound transmission performed at the angle closest to the ultrasound transmission direction used for receiving the reflected wave from which the determined image was generated, as the third ultrasound image. For example, the selecting unit 18b selects the image obtained as a result of the brightness adjusting process performed by the adjusting unit 18e on the ultrasound image corresponding to the angle "α4" shown in FIG. 3, as the third ultrasound image.

According to the second embodiment in which the third ultrasound image is selected out of the group of third ultrasound images on which the brightness adjusting process has been performed, because the possibility that multiple reflection artifacts are reduced is high, it is also acceptable to configure the selecting unit 18b so as to select the image having the maximum frequency of appearance of brightness levels that are equal to or higher than the predetermined threshold value, as the third ultrasound image. In that situation, for example, the selecting unit 18b selects the image obtained as a result of the brightness adjusting process performed by the adjusting unit 18e on the ultrasound image corresponding to the angle "α3" shown in FIG. 3, as the third ultrasound image.

Further, the extracting unit 18c included in the image generation controlling unit 181 according to the second embodiment extracts a puncture needle area from the third ultrasound image by using the method explained in the first embodiment, i.e., the extraction method using an extraction-purpose threshold value or the straight-line extraction method.

Further, the image generating unit 14 generates a needle image, so that the image synthesizing unit 16 generates a synthesized image. The synthesized image is then displayed on the monitor 2 by the display controlling unit 18d. As explained above, the image generation controlling unit 181 according to the second embodiment generates the needle image by analyzing the brightness distributions, while using as a target the group of third ultrasound images that are based on the analysis results obtained by analyzing the brightness distribution of each member of the group of second ultrasound images.

The process performed by the ultrasound diagnosis apparatus according to the second embodiment is the same as the process performed by the ultrasound diagnosis apparatus according to the first embodiment explained with reference to FIG. 6, except that the adjusting unit 18e generates, after step S103, the group of third ultrasound images by performing the brightness adjusting process on the group of second ultrasound images and that the third ultrasound image is selected out of the group of third ultrasound images at step S104; thus, the explanation thereof will be omitted. In addition, another arrangement is acceptable in which the display controlling unit 18d exercises control so that any of the first ultrasound image, the third ultrasound image, and the group of third ultrasound images is displayed together with the synthesized image, while positioned next to each other. Further, in the second embodiment also, the arrangement is acceptable in which the first scanning process and the second scanning process are sequentially performed in parallel with the processes at steps S103 through S107.

As explained above, according to the second embodiment, the adjusting unit 18e generates the group of third ultrasound images in which the brightness levels of the entirety of each of the ultrasound images are substantially uniform, by performing the brightness adjusting process on the group of second ultrasound images generated by the image generating unit 14. Further, the selecting unit 18b selects the third ultrasound image out of the group of third ultrasound images.

In other words, according to the second embodiment, it is possible to generate the needle image from the ultrasound images on which the brightness adjusting process has been performed.

In a third embodiment, an example will be explained in which a process to select a third ultrasound image is performed, after an image processing process using the first ultrasound image is performed on the group of second ultrasound images.

The controlling unit 18 according to the third embodiment is configured to be similar to the controlling unit 18 according to the first embodiment explained with reference to FIG. 1. In the third embodiment, however, the process performed by the selecting unit 18b included in the image generation controlling unit 181 is different from the processes in the first and the second embodiments. In the following sections, the third embodiment will be explained, while a focus is placed on the difference. In the third embodiment also, like in the first and the second embodiments, the first ultrasound image and the group of second ultrasound images are generated after the first scanning process and the second scanning process are performed.

Figure 9:
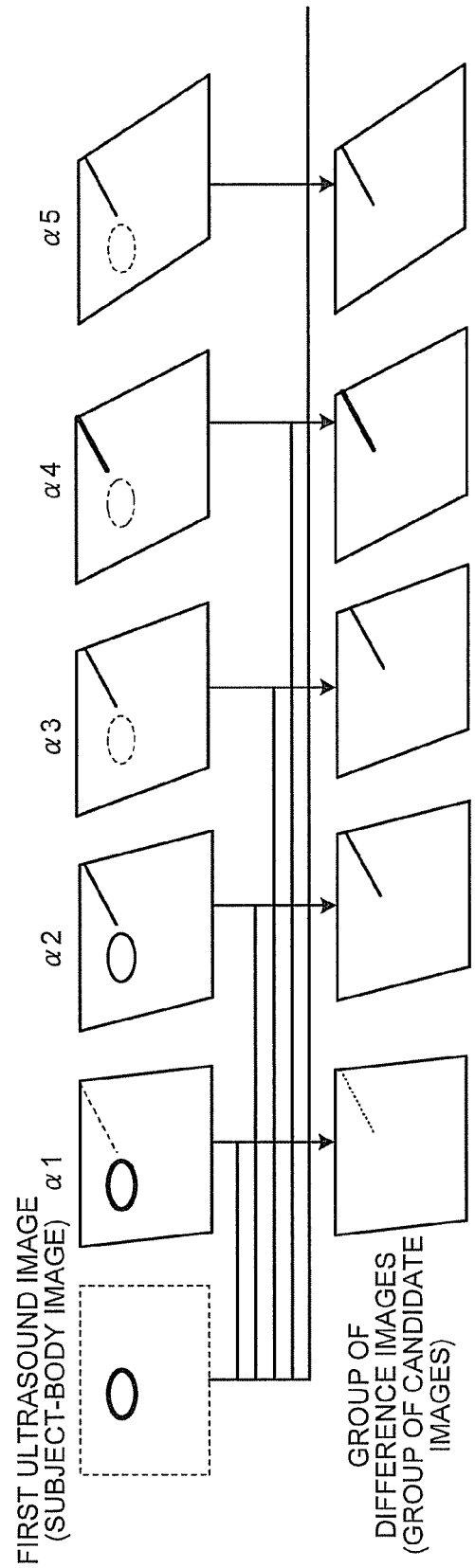
FIGS. 9 and 10 are drawings for explaining a selecting unit according to a third embodiment.
Figure 10:
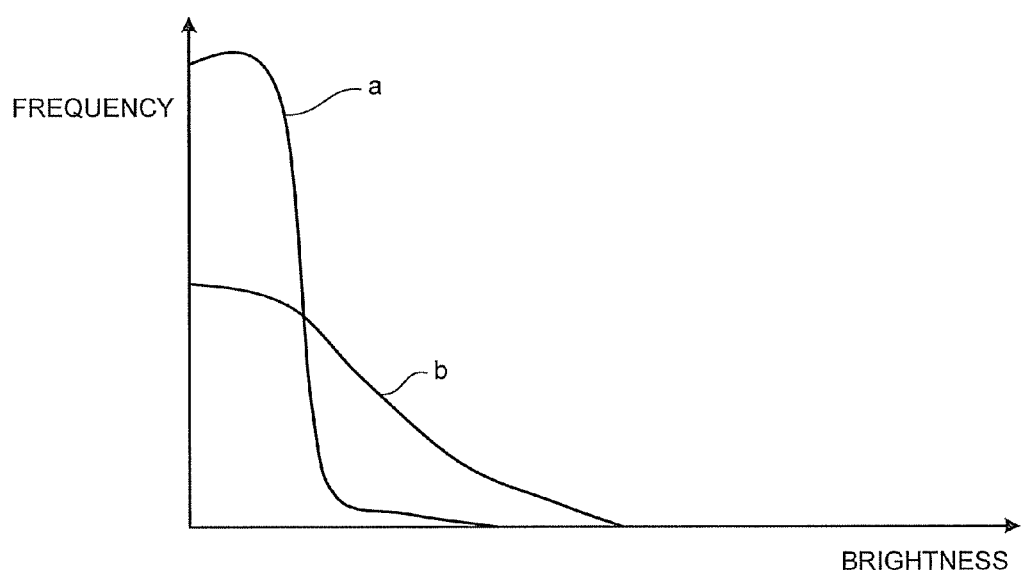

The image generation controlling unit 181 according to the third embodiment controls the image generating unit 14 so as to generate a needle image in which the puncture needle 1b is rendered with a high level of brightness, based on an analysis result obtained by analyzing the brightness distribution of each member of a group of images based on the first ultrasound image and the group of second ultrasound images. In other words, the selecting unit 18b included in the image generation controlling unit 181 according to the third embodiment selects a third ultrasound image out of the group of images based on the first ultrasound image and the group of second ultrasound images. More specifically, the selecting unit 18b according to the third embodiment controls the image generating unit 14 so as to generate a group of difference images by subtracting the first ultrasound image from each member of the group of second ultrasound images and further selects the third ultrasound image out of the group of difference images. FIGS. 9 and 10 are drawings for explaining the selecting unit according to the third embodiment.

Under the control of the selecting unit 18b, the image generating unit 14 according to the third embodiment subtracts the first ultrasound image (the subject-body image) from the group of second ultrasound images respectively corresponding to the angles "α1, α2, α3, α4, α5, . . . ", as shown in FIG. 9. In other words, the image generating unit 14 generates a difference image corresponding to each of the angles "α1, α2, α3, α4, α5, . . . ". As a result, the image generating unit 14 generates the group of difference images that serve as a group of candidate images. Further, the selecting unit 18b according to the third embodiment selects the third ultrasound image by performing a brightness analysis on the group of difference images. In the following sections, a predetermined condition used for selecting the third ultrasound image according to the third embodiment will be explained.

First, like in the first and the second embodiments, the selecting unit 18b generates a histogram (a brightness curve) indicating the brightness distribution of each of the difference images. In this situation, there is a high possibility that only the puncture needle 1b is extracted into each of the difference images. In other words, in a difference image in which the puncture needle 1b is rendered clearly, because a high brightness area appears only in a certain part, the brightness curve has a large distribution of low brightness levels and a small distribution of high brightness levels, as shown by a curve "a" in FIG. 10. In contrast, in a difference image in which the puncture needle 1b is rendered unclearly, because a medium brightness area appears only in a certain part, the brightness curve has a large distribution of low brightness levels and medium brightness levels, as shown by a curve "b" in FIG. 10.

For this reason, the selecting unit 18b selects one of the difference images that exhibits a brightness curve like the curve "a" in FIG. 10, as the third ultrasound image. For example, the selecting unit 18b selects the difference image generated by subtracting the first ultrasound image from the ultrasound image corresponding to the angle "α3" shown in FIG. 9, as the third ultrasound image.

Further, the extracting unit 18c included in the image generation controlling unit 181 according to the third embodiment extracts the entire third ultrasound image selected by the selecting unit 18b as a puncture needle area. In other words, in the third embodiment, the third ultrasound image itself is used as a needle image.

Alternatively, another arrangement is acceptable in which the extracting unit 18c according to the third embodiment extracts a high brightness area within the third ultrasound image selected by the selecting unit 18b, as a puncture needle area. In other words, it is acceptable if the extracting unit 18c according to the third embodiment extracts the puncture needle area from the third ultrasound image, by using an extraction method that uses an extraction-purpose threshold value or a straight-line extraction method. In that situation, the image generating unit 14 generates a needle image by using the puncture needle area, under the control of the extracting unit 18c, like in the first embodiment.

The operator is able to select whether the entire third ultrasound image is extracted as a puncture needle area or the high brightness area within the third ultrasound image is extracted as a puncture needle area.

Next, a process performed by an ultrasound diagnosis apparatus according to the third embodiment will be explained, with reference to FIG. 11. FIG. 11 is a flowchart for explaining the process performed by the ultrasound diagnosis apparatus according to the third embodiment.

As shown in FIG. 11, the ultrasound diagnosis apparatus according to the third embodiment judges whether a puncture mode has been started (step S201). In this situation, if the puncture mode has not been started (step S201: No), the ultrasound diagnosis apparatus according to the third embodiment is in a standby state until the puncture mode is started.

On the contrary, if the puncture mode has been started (step S201: Yes), the scan controlling unit 18a controls the ultrasound probe 1 so as to perform the first scanning process and the second scanning process (step S202).

After that, the image generating unit 14 generates a first ultrasound image (a subject-body image) and a group of second ultrasound images (a group of candidate images) (step S203). Under the control of the selecting unit 18b, the image generating unit 14 further generates a group of difference images by subtracting the first ultrasound image from each member of the group of second ultrasound images (step S204).

Subsequently, the selecting unit 18b selects a third ultrasound image out of the group of difference images (step S205). More specifically, the selecting unit 18b selects one of the difference images exhibiting such a brightness curve that has high frequency of appearance of low brightness levels and low frequency of appearance of high brightness levels, as the third ultrasound image.

After that, the extracting unit 18c extracts the entire third ultrasound image as a puncture needle area, so that the image generating unit 14 generates the third ultrasound image as a needle image (step S206). Alternatively, another arrangement is acceptable in which the extracting unit 18c extracts a puncture needle area from the third ultrasound image, by using an extraction-purpose threshold value or a straight-line extraction method, so that the image generating unit 14 generates a needle image by using the puncture needle area.

Subsequently, the image synthesizing unit 16 generates a synthesized image by synthesizing together the first ultrasound image and the needle image (step S207). As a result, a synthesized image corresponding to one frame has been generated.

Further, the display controlling unit 18d exercises control so that the synthesized image is displayed on the monitor 2 (step S208), and it is then judged whether the puncture mode has ended (step S209). In this situation, if the puncture mode has not ended (step S209: No), the ultrasound diagnosis apparatus returns to step S202 and exercises control so that a scanning process is performed so as to generate a synthesized image corresponding to the next frame.

On the contrary, if the puncture mode has ended (step S209: Yes), the ultrasound diagnosis apparatus ends the process. Another arrangement is acceptable in which the display controlling unit 18d exercises control so that any of the first ultrasound image, the third ultrasound image, and the group of difference images is displayed together with the synthesized image, while positioned next to each other. Also, in the example described above, the judgment of whether the puncture mode has ended is made after the synthesized image is displayed at step S208; however, it is acceptable to configure the third embodiment so that the judgment of whether the puncture mode has ended is made after the first scanning process and the second scanning process are performed at step S202. In other words, the arrangement is acceptable in which the first scanning process and the second scanning process are sequentially performed in parallel with the processes at steps S203 through S208.

As explained above, in the third embodiment, the selecting unit 18b controls the image generating unit 14 so as to generate the group of difference images by subtracting the first ultrasound image from each member of the group of second ultrasound images and further selects the third ultrasound image out of the group of difference images. After that, the extracting unit 18c extracts the entire third ultrasound image selected by the selecting unit 18b or the high brightness area within the third ultrasound image, as the puncture needle area.

In other words, in the third embodiment, the third ultrasound image is selected out of the group of difference images in each of which the information about the tissue in the subject's body is reduced. As a result, according to the third embodiment, it is possible to further improve the visibility of the puncture needle 1b, compared to the example in which the third ultrasound image is selected out of the group of images generated by performing an oblique scanning process. Also, in the first and the second embodiments described above, it is acceptable to extract the entire third ultrasound image as a puncture needle area, if the effect of artifacts on the tissue in the subject's body rendered in the third ultrasound image is small.

As a fourth embodiment, an example will be explained in which the brightness adjusting process explained in the second embodiment is performed with the third embodiment.

The controlling unit 18 according to the fourth embodiment is configured by adding the adjusting unit 18e explained in the second embodiment to the controlling unit 18 according to the third embodiment. In other words, the configuration of the controlling unit 18 according to the fourth embodiment is the same as that of the controlling unit 18 shown in FIG. 7.

Figure 12A:
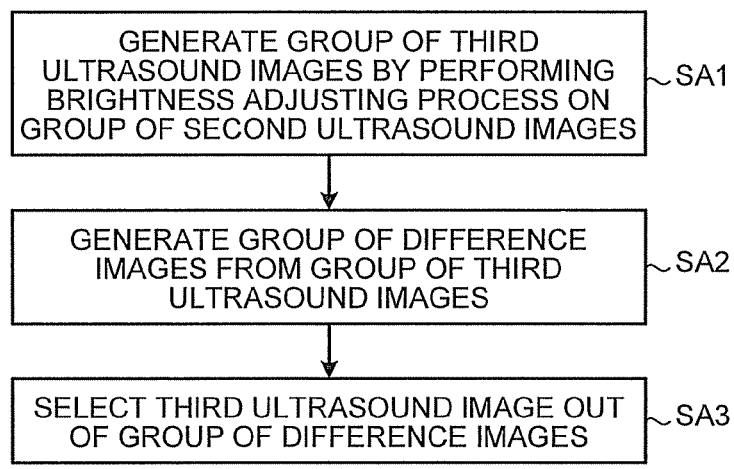
FIGS. 12A and 12B are drawings for explaining a process performed by a controlling unit according to a fourth embodiment.
Figure 12B:
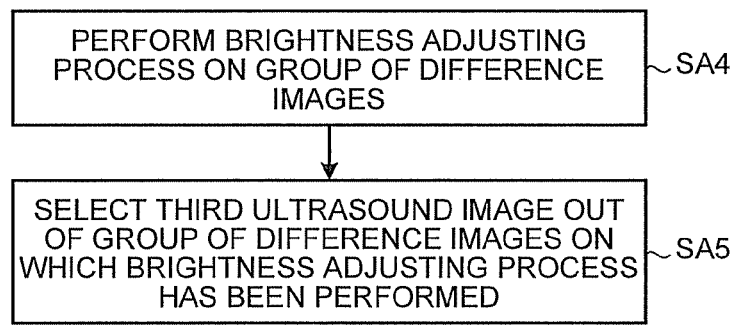

More specifically, in the fourth embodiment also, like in the first to the third embodiments, the first ultrasound image and the group of second ultrasound images are generated after the first scanning process and the second scanning process are performed. FIGS. 12A and 12B are drawings for explaining a process performed by the controlling unit according to the fourth embodiment.

Further, in the fourth embodiment, like in the second embodiment, the adjusting unit 18e generates a group of third ultrasound images in which the brightness levels of the entirety of each of the ultrasound images are substantially uniform, by performing the brightness adjusting process on the group of second ultrasound images (step SA1 shown in FIG. 12A).

After that, in the fourth embodiment, unlike in the third embodiment, the image generating unit 14 generates, under the control of the selecting unit 18b, a group of difference images from the group of third ultrasound images (step SA2 shown in FIG. 12A). In other words, the image generating unit 14 generates the group of difference images by subtracting each member of the group of third ultrasound images from the first ultrasound image.

Subsequently, in the fourth embodiment, a third ultrasound image is selected out of the group of difference images generated by using the group of third ultrasound images (step SA3 shown in FIG. 12A). In other words, in the example shown in FIG. 12A, the selecting unit 18b controls the image generating unit 14 so as to generate the group of difference images from the group of third ultrasound images and further selects the third ultrasound image out of the group of difference images. In this situation, the predetermined condition used for selecting the third ultrasound image in the example shown in FIG. 12A is the selecting condition explained in the third embodiment.

As explained above, in the fourth embodiment, the processes at steps SA1 through SA3 shown in FIG. 12A are performed, in place of the processes at steps S204 and S205 explained with reference to the flowchart in FIG. 11.

As a result, according to the fourth embodiment, because the image quality of the group of difference images out of which the third ultrasound image is selected is improved, it is possible to further improve the visibility of the puncture needle 1b compared to the third example.

It should be noted that, however, as mentioned earlier, in actual ultrasound images, the same site is seldom rendered with the same level of brightness by performing the oblique scanning processes, even if the brightness adjusting process is performed on the entirety of each image during the image acquiring process. Accordingly, there is a possibility that a difference image generated by using the third ultrasound image on which the brightness adjusting process has been performed may contain some areas in which the tissue in the subject's body that failed to be eliminated is rendered. For this reason, it is acceptable to configure the fourth embodiment so as to further include the process described below, as a modification example.

First, the adjusting unit 18e further performs a brightness adjusting process on the group of difference images (step SA4 shown in FIG. 12B). More specifically, the adjusting unit 18e further performs the brightness adjusting process to make the brightness levels of the entirety of each of the difference images substantially uniform, on the group of difference images generated by the image generating unit 14. In other words, the adjusting unit 18e performs the brightness adjusting process that was performed on the group of second ultrasound images, also on the group of difference images. With this arrangement, it is possible to eliminate residue areas showing the tissue in the subject's body that are contained in the difference images.

Alternatively, another arrangement is acceptable in which the adjusting unit 18e performs a brightness adjusting process on the group of difference images, by replacing any brightness level equal to or lower than a second threshold value with a predetermined value. For example, the second threshold value is set by referring to the brightness levels corresponding to the residues showing the tissue in the subject's body. Further, for example, the adjusting unit 18e replaces each of the brightness levels equal to or lower than the second threshold value with "0". With this arrangement also, it is possible to eliminate the residue areas showing the tissue in the subject's body that are contained the difference images.

After that, the selecting unit 18b selects a third ultrasound image out of the group of difference images on which the brightness adjusting process has been performed by the adjusting unit 18e (step SA5 shown in FIG. 12B). In this situation, the predetermined condition used for selecting the third ultrasound image in the example shown in FIG. 12B is the selecting condition explained in the third embodiment.

As explained above, in the modification example of the fourth embodiment, steps SA1 and SA2 shown in FIG. 12A and steps SA4 and SA5 shown in FIG. 12B are sequentially performed, in place of the processes at steps S204 and S205 explained with reference to the flowchart in FIG. 11.

As a result, in the modification example of the fourth embodiment, the group of difference images from which the third ultrasound image is selected has a lower possibility of having the residues showing the tissue in the subject's body rendered. Thus, it is possible to further improve the visibility of the puncture needle 1b, compared to the examples described above. Like in the third embodiment, in the fourth embodiment and the modification example of the fourth embodiment, it is acceptable if the entire third ultrasound image is extracted as a puncture needle area or if a high brightness area within the third ultrasound image is extracted as a puncture needle area.

Figure 13:
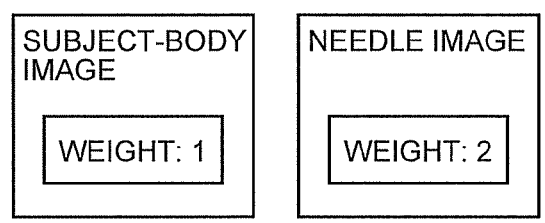
FIG. 13 is a drawing for explaining a modification example of the image synthesizing unit.

It is acceptable to configure the image synthesizing unit 16 according to any of the first to the fourth embodiments described above, so as to generate the synthesized image by superimposing the first ultrasound image (the subject-body image) and the needle image with each other simply in a one-on-one manner, or so as to perform a synthesizing process described below. FIG. 13 is a drawing for explaining a modification example of the image synthesizing unit.

More specifically, the image synthesizing unit 16 generates a synthesized image by changing the weights used for synthesizing together the first ultrasound image and the needle image. For example, as shown in FIG. 13, the image synthesizing unit 16 generates a synthesized image in which the puncture needle 1b is emphasized, by setting the weight for the subject-body image to "1" and setting the weight for the needle image to "2". In this situation, the operator is able to arbitrarily change the weight for each of the images and is able to change the weights, for example, even during medical practice. In other words, when the operator wishes to refer to a synthesized image in which the puncture needle 1b is emphasized, the operator increases the weight for the needle image, whereas when the operator wishes to refer to a synthesized image in which the tissue in the subject's body is emphasized, the operator increases the weight for the subject-body image. For example, the weight for each of the images is set via the input device 3.

Another arrangement is also acceptable in which the image synthesizing unit 16 generates a plurality of synthesized images by varying the weights. For example, it is acceptable to configure the image synthesizing unit 16 so as to generate two synthesized images in which the weights between the subject-body image and the needle image is "1:2" and "2:1", respectively. Further, it is also acceptable to configure the image synthesizing unit 16 so as to additionally generate a synthesized image in which the subject-body image and the needle image are synthesized together with "1:1" weights, even when it is requested that the image synthesizing unit 16 should generate a synthesized image in which the weights are changed. In that situation, the display controlling unit 18d displays the plurality of synthesized images so as to be positioned next to one another.

According to the modification example described above, it is possible to display, in response to the request from the operator (the medical doctor), the synthesized images in which one of the tissue in the subject's body and the puncture needle 1b is emphasized. It is therefore possible to further aid the puncture process performed by the operator.

Further, in the first to the fourth embodiments described above, the example is explained in which the plurality of ultrasound transmission directions used for performing the second scanning process are fixed; however, it is also acceptable to perform the second scanning process according to any of the first to the fourth embodiments, as in a modification example described below.

Figure 14A:
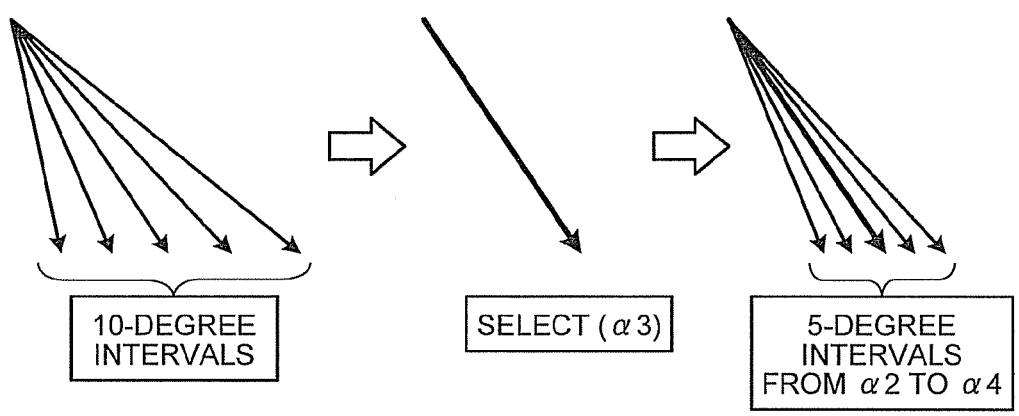
FIGS. 14A and 14B are drawings for explaining a modification example of the scan controlling unit.
Figure 14B:
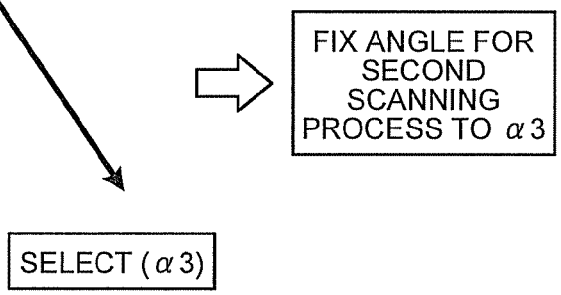

Specifically, the scan controlling unit 18a according to this modification example changes the ultrasound transmission condition used in the second scanning process, based on the ultrasound transmission direction used for receiving the reflected wave from which the third ultrasound image selected by the selecting unit 18b was generated. FIGS. 14A and 14B are drawings for explaining the modification example of the scan controlling unit.

In one example, the scan controlling unit 18a first causes a second scanning process to be performed in a predetermined angle range (a range from the angle "B-B$_0$" to the angle "B-B$_1$") at 10-degree intervals, as shown in FIG. 14A. In this situation, let us assume that, for example, the selecting unit 18b has selected the third ultrasound image generated by performing the oblique scanning process corresponding to the angle "α3", as shown in FIG. 14A. In that situation, for example, the scan controlling unit 18a determines the angle "α3" to be a candidate angle used for generating a needle image as shown in FIG. 14A and further causes a second scanning process to be performed again while arranging "the intervals from α2 to α4 to be 5-degree intervals" centered around the angle "α3".

Further, the selecting unit 18b selects a third ultrasound image out of the group of images generated by performing the second scanning process again. It is also acceptable to repeatedly perform the second scanning process three or more times. For example, an arrangement is acceptable in which the second scanning process is repeatedly performed a predetermined number of times, while gradually decreasing the angular intervals and the angle range.

According to the modification example described above, it is possible to select the oblique angle optimal for generating the needle image, with a high level of precision.

The modification applied to the second scanning process is not limited to the example described above in which the second scanning process is repeatedly performed for generating the synthesized image corresponding to one frame. For instance, another arrangement is acceptable in which the angular intervals and the angle range in the second scanning process performed for generating a new frame are decreased, based on the oblique angle used for generating the third ultrasound image selected in the immediately preceding the frame. With this arrangement, it is possible to reduce the processing load required in the synthesized image generating process. In particular, when the brightness adjusting process is performed, it is possible to reduce the quantity of images on which the brightness adjusting process is performed.

Further, the second scanning process does not necessarily have to be performed in a plurality of directions. For example, an arrangement is acceptable in which the scan controlling unit 18a determines the ultrasound transmission direction used for receiving the reflected wave from which the third ultrasound image selected by the selecting unit 18b was generated, to be a second direction that serves as the ultrasound transmission direction used for performing the second scanning process. For example, let us assume that, as shown in FIG. 14B, the selecting unit 18b has selected the third ultrasound image generated by performing the oblique scanning process corresponding to the angle "α3". In that situation, as shown in FIG. 14B, it is acceptable to configure the scan controlling unit 18a so as to determine, for the following frames, the ultrasound transmission direction corresponding to the angle "α3" to be the second direction and so as to perform the second scanning process while fixing the ultrasound transmission direction to the second direction. When the angle used in the second scanning process is fixed, the process performed by the selecting unit 18b is skipped so that a needle image is generated from the image generated by performing an oblique scanning process corresponding to the angle "α3" as a result of the process performed by the extracting unit 18c.

In this situation, the transition from the second scanning process performed in a plurality of directions to the second scanning process performed in a single direction can be roughly divided into the various patterns described below: In a first pattern, the oblique scan angle is determined in the first frame, so that a transition is made from the second scanning process performed in a plurality of directions, to the second scanning process performed in a single direction. In a second pattern, the second scanning process is performed in a plurality of directions for two or more frames, so that if the oblique scan angle selected in each of the frames is within a predetermined range, a transition is made from the second scanning process performed in the plurality of directions, to the second scanning process performed in a single direction. In that situation, it is possible to use an average value or a median as the fixed oblique scan angle.

In these examples described above, it is also possible to reduce the processing load required in the synthesized image generating process.

Further, it is also acceptable to configure the scan controlling unit 18a so as to employ both the second scanning process performed in a plurality of directions and the second scanning process performed in a single direction, in the manner described below: After determining the second direction, the scan controlling unit 18a causes the selecting unit 18b to perform again, at a predetermined time, the process of selecting a third ultrasound image, while arranging the ultrasound transmission directions used in the second scanning process to be a plurality of directions. Further, the scan controlling unit 18a determines the ultrasound transmission direction used for receiving the reflected wave from which the third ultrasound image selected by the selecting unit 18b was generated, as a new second direction. In this situation, the predetermined time at which the second direction is updated may be a point in time specified by the operator or may be a point in time when a period of time set in advance has elapsed. For example, the scan controlling unit 18a exercises control so that, even after a transition is made to the second scanning process performed in the single direction (the second direction), the second scanning process is performed in a plurality of directions, either once or two or more times, at predetermined intervals (e.g., once in every five frames). In this manner, the scan controlling unit 18a determines again the oblique scan angle (the new second direction) used for performing the second scanning process in a single direction.

In the examples described above, it is possible to reduce the processing load required in the synthesized image generating process, while sequentially updating the optimal oblique angle used for generating the needle image.

In the description above, the examples in which one third ultrasound image is selected are explained; however, in some situations, there may be a plurality of images that satisfy the "predetermined condition" explained in the first to the fourth embodiments. In the following sections, a process to be performed when the selecting unit 18b has selected a plurality of images satisfying the predetermined condition will be explained.

When having selected a plurality of images satisfying the predetermined condition, the selecting unit 18b controls the image generating unit 14 so as to generate an addition image obtained by adding together the selected plurality of images. For example, the image generating unit 14 generates the addition image by adding together the plurality of images selected by the selecting unit 18b. Alternatively, for example, the image generating unit 14 generates the addition image by calculating an arithmetic mean of the plurality of images selected by the selecting unit 18b. Further, it is also acceptable to configure the selecting unit 18b so as to, for example, set a weight used for generating the addition image for each of the selected plurality of images, based on a degree of matching with the predetermined condition for each of the selected images.

Further, the extracting unit 18c performs the process to extract a puncture needle area while using the addition image as the third ultrasound image. By using the addition image, it is possible to generate a needle image in which the puncture needle 1b is further emphasized.

When a plurality of third ultrasound images have been selected, it is acceptable to configure the scan controlling unit 18a so as to change the ultrasound transmission condition used in the second scanning process, based on the plurality of ultrasound transmission directions used for receiving the reflected waves from which the plurality of third ultrasound images were generated. For example, when the oblique scan angles corresponding to three selected images are "α3, α4, and α5", it is acceptable to configure the scan controlling unit 18a to cause a second scanning process to be performed, while using the three ultrasound transmission directions defined by the angles "α3, α4, and α5" as "three 'second directions'". Further, when the second scanning process is performed while fixing the ultrasound transmission directions to the plurality of second directions, it is acceptable to perform again a process to update the ultrasound transmission directions used in the second scanning process, at a predetermined time. In that situation, the second directions may be updated to a single direction or to a plurality of directions.

Alternatively, it is also acceptable to configure the selecting unit 18b so as to, after having selected a plurality of images satisfying the predetermined condition, further select one of the selected plurality of images. For example, it is acceptable to configure the selecting unit 18b so as to notify the extracting unit 18c of the one of the images arbitrarily selected out of the selected plurality of images, as a third ultrasound image. Alternatively, it is acceptable to configure the selecting unit 18b so as to, for example, notify the extracting unit 18c of the image that best matches the predetermined condition among the selected plurality of images, as a third ultrasound image.

Further, if the selecting unit 18b has selected a plurality of images satisfying the predetermined condition, but is unable to further select an image that best matches the predetermined condition from among the selected plurality of images, it is acceptable configure the scan controlling unit 18a so as to exercise control in the following manner: The scan controlling unit 18a causes the second scanning process to be performed again with a decreased angular interval and a decreased angle range, once or two or more times, as explained with reference to FIG. 14A, until the selecting unit 18b selects one third ultrasound image. Further, the selecting unit 18b selects the image that best matches the predetermined condition out of the group of images generated from the second scanning process performed again, as a third ultrasound image.

It is possible to realize the controlling method explained in any of the first to the fourth embodiments and the modification examples by causing a computer such as a personal computer or a workstation to execute a control program prepared in advance. It is possible to distribute the control program via a network such as the Internet. Further, it is also possible to record the control program onto a computer-readable non-temporary recording medium such as a hard disk, a flexible disk (FD), a Compact Disk Read-Only memory (CD-ROM), a Magneto-Optical (MO) disk, a Digital Versatile Disk (DVD), a flash memory like a Universal Serial Bus (USE) memory and a Secure Digital (SD) card, or the like, so that a computer reads the control program from the non-temporary recording medium and executes the control program.

As explained above, according to the first to the fourth embodiments and the modification examples, it is possible to improve the visibility of both the tissue in the subject's body and the puncture needle.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
a scan controlling circuit configured to, when performing an ultrasound scanning process on a subject into whom a puncture needle has been inserted, cause an ultrasound probe to perform a first scanning process by transmitting an ultrasound wave in a first direction with respect to a surface of a vibrator for a purpose of taking an image of a tissue of the subject and a second scanning process by transmitting an ultrasound wave in each of a plurality of directions with respect to the surface of the vibrator;
an image generating circuit configured to generate a first ultrasound image by using a reflected wave received by the ultrasound probe during the first scanning process and to generate a group of second ultrasound images that are ultrasound images corresponding to the plurality of directions by using reflected waves received by the ultrasound probe during the second scanning process;
a selecting circuit configured to have a function of analyzing a brightness distribution within each image and to select an image of which an analysis result satisfies a predetermined condition out of an analyzed group of images, as a third ultrasound image in which the puncture needle is rendered with a high level of brightness, wherein the analyzed group of images is a group of images based on the first ultrasound image and the group of second ultrasound images or the group of second ultrasound images;
an extracting circuit configured to extract a high brightness area having brightness levels equal to or higher than an extraction-purpose threshold within the third ultrasound image as the puncture needle area, configured to notify the image generating circuit of coordinates of the high brightness area within the third ultrasound image, and configured to control the image generating circuit to generate a needle image by replacing brightness levels in an area other than the high brightness area within the third ultrasound image by a predetermined value;
an image synthesizing circuit configured to generate a synthesized image by synthesizing together the first ultrasound image and the needle image generated by the image generating circuit; and
a display controlling circuit configured to exercise control so that the synthesized image generated by the image synthesizing circuit is displayed on a predetermined display unit.

2. The ultrasound diagnosis apparatus according to claim 1, wherein out of the group of second ultrasound images, the selecting circuit selects an image generated from a reflected wave received in such an ultrasound transmission performed at an angle closest to an ultrasound transmission direction used for receiving a reflected wave from which an image having a maximum frequency of appearance of pixels each having a brightness level equal to or higher than a predetermined threshold value was generated, as the third ultrasound image.

3. The ultrasound diagnosis apparatus according to claim 1, further comprising: an adjusting circuit configured to generate a group of third ultrasound images in which brightness levels of an entirety of each of the ultrasound images are substantially uniform, by performing a brightness adjusting process on the group of second ultrasound images generated by the image generating circuit, wherein
the selecting circuit selects the third ultrasound image out of the group of third ultrasound images.

4. The ultrasound diagnosis apparatus according to claim 1,
wherein the selecting circuit controls the image generating circuit so as to generate a group of difference images by subtracting the first ultrasound image from each member of the group of second ultrasound images and selects the third ultrasound image out of the group of difference images.

5. The ultrasound diagnosis apparatus according to claim 4, further comprising:
an adjusting circuit configured to generate a group of third ultrasound images in which brightness levels of an entirety of each of the ultrasound images are substantially uniform, by performing a brightness adjusting process on the group of second ultrasound images generated by the image generating circuit, wherein
the selecting circuit controls the image generating circuit so as to generate the group of difference images from the group of third ultrasound images and selects the third ultrasound image out of the group of difference images.

6. The ultrasound diagnosis apparatus according to claim 5, wherein the adjusting circuit further performs, on the group of difference images generated by the image generating circuit, a brightness adjusting process to make brightness levels of an entirety of each of the difference images substantially uniform or a brightness adjusting process to replace any brightness level equal to or lower than a second threshold value with a predetermined value, and
the selecting circuit selects the third ultrasound image out of the group of difference images on which the brightness adjusting process has been performed by the adjusting circuit.

7. The ultrasound diagnosis apparatus according to claim 1, wherein the image synthesizing circuit generates the synthesized image by changing weights used for synthesizing together the first ultrasound image and the needle image.

8. The ultrasound diagnosis apparatus according to claim 1, wherein
when the selecting circuit has selected a plurality of images satisfying the predetermined condition, the selecting circuit controls the image generating circuit so as to generate an addition image obtained by adding together the selected plurality of images, and
the extracting circuit extracts the puncture needle area, while using the addition image as the third ultrasound image.

9. The ultrasound diagnosis apparatus according to claim 1, wherein the scan controlling circuit changes an ultrasound transmission condition used for performing the second scanning process, based on an ultrasound transmission direction used for receiving a reflected wave from which the third ultrasound image selected by the selecting circuit was generated.

10. The ultrasound diagnosis apparatus according to claim 9, wherein the scan controlling circuit determines the ultrasound transmission direction used for receiving the reflected wave from which the third ultrasound image selected by the selecting circuit was generated, as a second direction that is an ultrasound transmission direction used for performing the second scanning process.

11. The ultrasound diagnosis apparatus according to claim 10, wherein
after determining the second direction, the scan controlling circuit causes, at a predetermined time, the selecting circuit to perform again a process to select the third ultrasound image while using the plurality of directions as ultrasound transmission directions used for performing the second scanning process, and
the scan controlling circuit determines an ultrasound transmission direction used for receiving a reflected wave from which the third ultrasound image selected by the selecting circuit was generated, as a new second direction.

12. A controlling method comprising:
a process performed by a scan controlling circuit to, when performing an ultrasound scanning process on a subject into whom a puncture needle has been inserted, cause an ultrasound probe to perform a first scanning process by transmitting an ultrasound wave in a first direction with respect to a surface of a vibrator for a purpose of taking an image of a tissue of the subject and a second scanning process by transmitting an ultrasound wave in each of a plurality of directions with respect to the surface of the vibrator;
a process performed by an image generating circuit to generate a first ultrasound image by using a reflected wave received by the ultrasound probe during the first scanning process and to generate a group of second ultrasound images that are ultrasound images corresponding to the plurality of directions by using reflected waves received by the ultrasound probe during the second scanning process;
a process performed by a selecting circuit, having a function of analyzing a brightness distribution within each image, to select an image of which an analysis result satisfies a predetermined condition out of an analyzed group of images, as a third ultrasound image in which the puncture needle is rendered with a high level of brightness, wherein the analyzed group of images is a group of images based on the first ultrasound image and the group of second ultrasound images or the group of second ultrasound images;
a process performed by an extractor to extract a high brightness area having brightness levels equal to or higher than an extraction-purpose threshold within the third ultrasound image as the puncture needle area, to notify the image generating circuit of coordinates of the high brightness area within the third ultrasound image, and to control the image generating circuit to generate a needle image by replacing brightness levels with predetermined value in area other than the high brightness area within the third ultrasound image by a predetermined value;
a process performed by an image synthesizing circuit to generate a synthesized image by synthesizing together the first ultrasound image and the needle image generated by the image generating circuit; and
a process performed by a display controlling circuit to exercise control so that the synthesized image generated by the image synthesizing circuit is displayed on a predetermined display unit.

* * * * *